(12) United States Patent
Reuter

(10) Patent No.: US 9,770,032 B2
(45) Date of Patent: Sep. 26, 2017

(54) COMPOSITIONS FOR STABILIZING BACILLUS SPORES AND METHODS OF USE THEREOF

(75) Inventor: Christopher J. Reuter, Parrish, FL (US)

(73) Assignee: Osprey Biotechnics, Inc., Sarasota, FL (US)

( * ) Notice: Subject to any disclaimer, the term of this patent is extended or adjusted under 35 U.S.C. 154(b) by 1965 days.

(21) Appl. No.: 12/658,920

(22) Filed: Feb. 17, 2010

(65) Prior Publication Data

US 2011/0200572 A1 Aug. 18, 2011

(51) Int. Cl.
*A01N 53/00* (2006.01)
*A01N 63/00* (2006.01)

(52) U.S. Cl.
CPC .................................. *A01N 63/00* (2013.01)

(58) Field of Classification Search
None
See application file for complete search history.

(56) References Cited

U.S. PATENT DOCUMENTS

| | | | |
|---|---|---|---|
| 5,733,355 A | 3/1998 | Hibino et al. | |
| 5,919,695 A | 7/1999 | Vedamuthu et al. | |
| 6,423,310 B1 | 7/2002 | Wilson et al. | |
| 6,589,524 B1 | 7/2003 | Douillet | |
| 6,830,459 B2 | 12/2004 | West | |
| 6,849,256 B1 * | 2/2005 | Farmer | 424/93.46 |
| 2003/0099624 A1 | 5/2003 | Porubcan | |
| 2005/0191206 A1 | 9/2005 | Buhr et al. | |
| 2008/0160134 A1 | 7/2008 | Hestekin et al. | |
| 2009/0047383 A1 | 2/2009 | Ogasawara et al. | |

OTHER PUBLICATIONS

Emmert et al. FEMS Microbiology Letters. 1999, 171, pp. 1-9.*
Russell, A.D., Bacterial Spores and Chemical Sporicidal Agents, Clinical Microbiology Reviews, Apr. 1990, vol. 3, No. 2, pp. 99-119.
Driks, A. (2002) Cellular and Mol. Life Sciences 59: 389-391.
Grossman, AD, and Losick, R. (1988) Proc. Natl. Acad. Sci. USA, 85: 4369-4373.
Waites, WM, and Wild DG (1970) J. General Microbiology, 61: 311-317.
Wong et al., Effects of Lactic Acid Bacteria and Organic Acids on Growth and Germination of *Bacillus cereus*, 1988, Appl. Env. Microbiol. 54(9): 2179-2184.
Rosenquist et al., The antimicrobial effect of organic acids, sour dough and nisin against *Bacillus subtilis* and *B. licheniformis* isolated from wheat bread, 1998, J. Applied Microbiol. 85(3): 621-631.

\* cited by examiner

*Primary Examiner* — Vera Afremova
(74) *Attorney, Agent, or Firm* — Butzel Long

(57) ABSTRACT

The invention provides methods for providing *Bacillus* spores for application to agricultural soil or plant material. The methods comprise suspending the *Bacillus* spores in a liquid consisting essentially of water and an organic acid, including acetic acid, wherein the acid lowers the pH so that the spores are inhibited from germination and growth; and so that growth of unwanted microorganisms in the suspension is prevented. Compositions formed according to the methods of the invention are also provided.

22 Claims, 1 Drawing Sheet

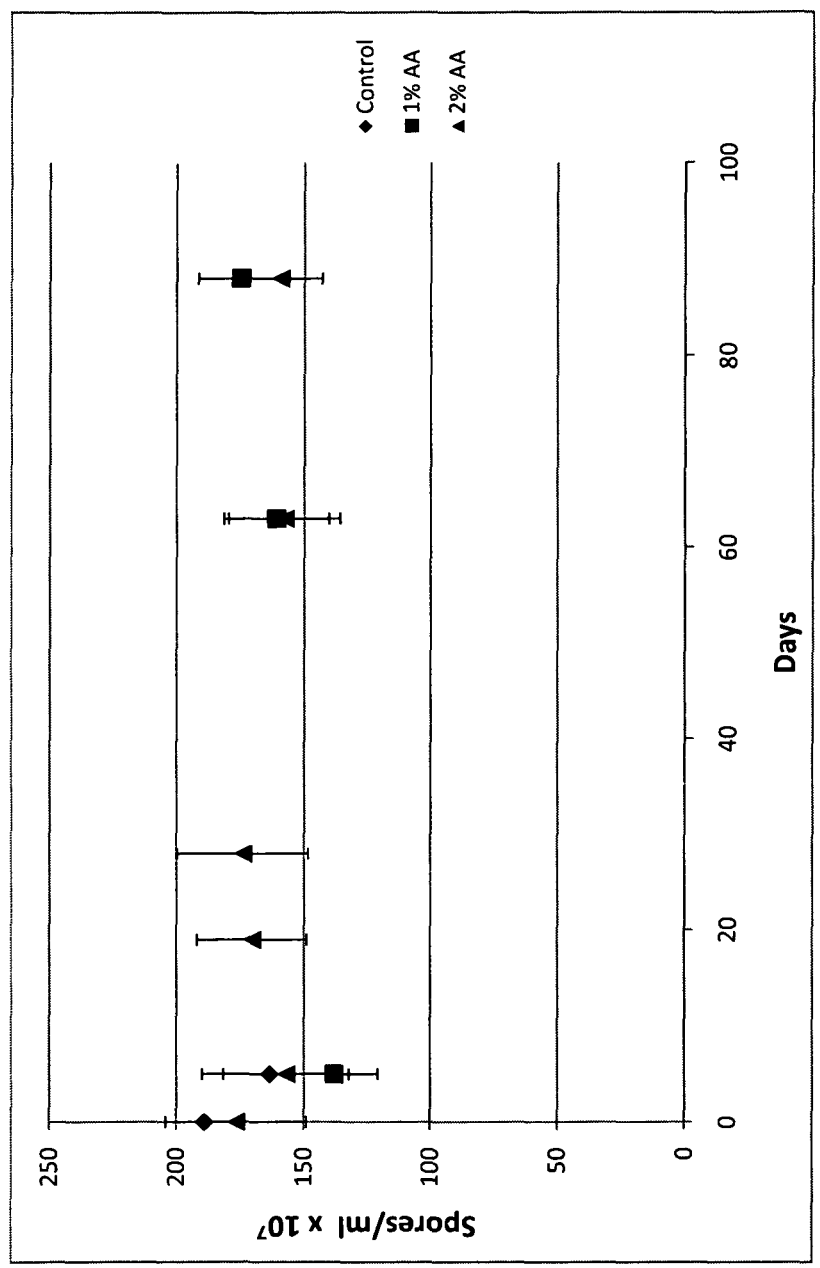

COMPOSITIONS FOR STABILIZING BACILLUS SPORES AND METHODS OF USE THEREOF

CROSS-REFERENCE TO RELATED APPLICATIONS

None.

STATEMENT REGARDING FEDERALLY SPONSORED RESEARCH OR DEVELOPMENT

None.

STATEMENT REGARDING GOVERNMENT RIGHTS

None.

FIELD OF THE INVENTION

The invention relates to methods and compositions for providing *Bacillus* spores in a liquid in which the germination and growth of the spores are inhibited, and spoilage is prevented. In various embodiments, the liquid consists essentially of water and acetic acid, preferably acetic acid from a fermentation.

BACKGROUND OF THE INVENTION

Bacterial cultures have wide industrial uses; including environmental and agricultural uses as bioremediation reagents, as alternatives to harmful chemicals such as certain pesticides, and as agents for improving plant and animal health. Industrial users of bacterial cultures include manufacturers of probiotics and prebiotics, bacterial seed coatings, and soil augmentation product manufacturers.

Particular species of the gram positive bacteria *Bacillus* have found uses in agriculture as antifungal agents. For example, U.S. Pat. No. 6,589,524 refers to the use of *B. cereus, B. amyloliquefaciens*, and *B. subtilis* for biological control of pathogenic fungi. U.S. Pat. No. 6,830,459 refers to application of *Bacillus*, including *B. subtilis* in combination with chitosanase inducers for preventing or treating microbial colonization and fungal growth. U.S. Pat. No. 6,423,310 refers to use of biological coatings that confer protective and curative effects for the control of postharvest decay. The coatings have antifungal properties and include chitosan salts, antagonistic organisms including yeast or bacteria such as *B. subtilis*, and a cation. Other uses of *Bacillus* have included uses of *Bacillus* preparations for soil conditioning, for enhancing fermentation of cellulosic materials, and as a deodorant for feces and urine of animals; as referred to in U.S. Pat. No. 5,733,355. U.S. Pat. No. 5,919, 695 refers to an atypical *B. subtilis* strain for use in controlling molds and other spoilage flora in various materials, particularly foods.

Sporulation in gram positive bacteria, including *Bacillus*, leads to formation of spores (endospores) which are dormant; and therefore desirable for industrial purposes including manufacturing, shipping, and storage. Activation of the dormant spores leads to germination and growth of active bacteria. Sporulation in *B. subtilis* has been classically viewed as a unicellular differentiation that occurs in response to nutritional starvation. More recently, in addition to complex morphological and metabolic changes, changes in the soluble protein profile of the bacterium, including identification of specific proteins associated with sporulation have been reported. For example, the extracellular differentiation factor A (EDF-A), a secreted factor, is reported to be required, in addition to starvation conditions, for efficient sporulation in *B. subtilis*. See Waites W M, and Wild D G (1970), J. General Microbiology, 61: 311-317; Grossman A D, and Losick R (1988) Proc. Natl. Acad. Sci. USA, 85: 4369-4373; Driks A (2002) Cellular and Mol. Life Sciences 59: 389-391.

SUMMARY OF THE INVENTION

In one aspect, the invention provides a method for providing *Bacillus* spores for application to agricultural soil or plant material, which comprises the step: suspending the *Bacillus* spores in a liquid consisting essentially of water and acetic acid, wherein the acetic acid lowers the pH so that the spores are inhibited from germination and growth.

In a related aspect, the invention provides a method for providing a *Bacillus* on agricultural soil or plant material, which comprises the steps: (a) suspending *Bacillus* spores in a liquid consisting essentially of water and acetic acid, wherein the acetic acid lowers the pH so that the spores are inhibited from germination and growth; and (b) neutralizing the liquid of step (a) to enable the spores to provide an enabled *Bacillus* and applying the enabled *Bacillus* to the soil or plant material.

In another, the invention provides a method for providing a *Bacillus* on agricultural soil or plant material, which comprises the steps: (a) preparing *Bacillus* spores in a minimal media effective to sporulate *Bacillus*; (b) separating said spores from said media; (c) optionally washing said spores; (d) suspending the spores from step (b) or (c) in a liquid consisting essentially of water and acetic acid, wherein the acetic acid lowers the pH so that the spores are inhibited from germination and growth; and (e) neutralizing the liquid of step (d) to enable the spores to provide an enabled *Bacillus* and applying the enabled *Bacillus* to the soil or plant material.

In a further related aspect, the invention provides a composition comprising *Bacillus* spores suspended in a liquid at a pH from about 3.8 to about 4.2, said liquid consisting essentially of water and acetic acid derived from vinegar; wherein in use of the composition, the pH is raised and used for application to plant material or soil.

In another, the invention provides a composition comprising *Bacillus* spores in a liquid consisting essentially of water and acetic acid; wherein said composition is formed by the process comprising the steps: (a) preparing *Bacillus* spores in a minimal media effective to sporulate *Bacillus*; (b) separating said spores from said media; (c) optionally washing said spores; and (d) suspending the spores from step (b) or (c) in a liquid consisting essentially of water and acetic acid, wherein the acetic acid lowers the pH so that the spores are inhibited from germination and growth.

In another aspect, the invention provides a method for providing *Bacillus* spores for application to agricultural soil or plant material, which comprises the step: suspending the *Bacillus* spores in a liquid consisting essentially of water and an organic acid, wherein the organic acid lowers the pH so that the spores are inhibited from germination and growth. In particular embodiment, the method further comprises neutralizing the liquid of the suspending step to enable the spores to provide an enabled *Bacillus* and applying the enabled *Bacillus* to the soil or plant material. In another, the method further comprises the steps: i) preparing *Bacillus* spores in a minimal media effective to sporulate *Bacillus*; ii)

separating said spores from said media; and iii) optionally washing said spores; wherein said steps (i), (ii), and (iii) are performed prior to the suspending step.

In another related aspect, the invention provides a composition comprising *Bacillus* spores in a liquid consisting essentially of water and an organic acid; wherein said composition is formed by the methods stated above.

In a further related aspect, the invention provides a method for providing *Bacillus* spores for application to agricultural soil or plant material, which comprises the steps: suspending the *Bacillus* spores in a liquid consisting essentially of water and an organic acid, wherein the organic acid lowers the pH so that the spores are inhibited from germination and growth; and transferring the suspension of the suspending step to a sealable container under aseptic conditions and sealing the container. In a particular embodiment, the method further comprises preparing *Bacillus* spores in a minimal media effective to sporulate *Bacillus*; separating said spores from said media; and optionally washing said spores prior to the suspending step. In another, the methods further comprise testing a sample of said suspension and thereby determining that the sample and the transferred suspension are acceptably free of unwanted microorganisms. In another, the unwanted organisms are selected from one or more of: coagulase positive *staphylococcus, Pseudomonas aeruginosa, Salmonella/Shigella* sp., coliforms, yeast, and mold.

In another related aspect, the invention provides an article of manufacture comprising a sealed container comprising *Bacillus* spores in a liquid consisting essentially of water and an organic acid; wherein said article is formed by the methods stated above and comprising a transferring step. In a particular embodiment, the article further comprises directions for use wherein said directions comprise directing the user to neutralize the liquid in said container.

In any aspect of the invention in which an organic acid is utilized, in a particular embodiment, the acid is acetic acid.

In any aspect of the invention comprising a suspending step, in a particular embodiment of the present invention, the pH in the suspending step is lowered to a pH from about 3.8 to about 4.2. In another, the acetic acid in said liquid in the suspending step is at a concentration of 1 to 5%. In another, the acetic acid is from a fermentation process to produce a vinegar used in the suspending step. In another, the acetic acid is from a 20 percent acetic acid vinegar which is used to lower the pH in the suspending step.

In any aspect of the invention comprising a preparing step, a suspending step, or in which the invention provides a composition comprising *Bacillus* spores, in a particular embodiment of the present invention, the *Bacillus* spores are *Bacillus subtilis*.

In any aspect of the invention in which the invention provides a method for providing *Bacillus* spores for application to agricultural soil or plant material, or in which the method provides an applying step, in a particular embodiment of the present invention, the plant material is a seed. In another, the applying is to soil. In another, the applying is to a plant.

In any aspect of the invention comprising a neutralizing step, in a particular embodiment of the present invention, the neutralizing is with a base selected from the group consisting of: sodium bicarbonate, potassium bicarbonate, sodium hydroxide, potassium hydroxide, calcium carbonate, and alkaline soil.

In any aspect of the invention comprising a separating step, in a particular embodiment of the present invention, the separating is by tangential flow filtration or centrifugation.

In another, the tangential flow filtration utilizes a filter from about 0.1 micron to less than 1 micron. In another, the centrifugation is performed at a force from about 3000 g to about 10,000 g.

BRIEF DESCRIPTION OF THE DRAWINGS

FIG. 1 depicts a time course study of *Bacillus subtilis* spore suspensions prepared according to the methods of the invention.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the drawings, examples, and appended claims.

Preservation of dormant *Bacillus* spores desirable for industrial purposes can be achieved by methods such as drying, freeze-drying, lyophilization, and the like; where the spore preparations are not stored in a liquid. However; such methods have the disadvantages of additional effort and cost in preparing the non-liquid preparations; and also of being prone to additional opportunities for contamination. As an alternative, preservation of bacterial liquid products, in particular those containing *Bacillus* endospores, has long been achieved by addition of biostatic and/or biocidal agents; as a means of inhibiting undesired bacterial growth in the products. However, uses of such agents and other biologically harmful chemicals are not desired for applications including environmental, agricultural, food, and feed applications.

Therefore, non-synthetic (organic) methods of stabilization, and inhibition of unwanted microbial growth in *Bacillus* spore liquid cultures are useful for applications in which synthetic chemicals, particularly biologically harmful chemicals are not desired; including environmental, agricultural, food, and feed applications.

The invention is related to compositions and methods for stabilization of liquid *Bacillus* spore suspensions; preferably by using acetic acid from a fermentation source. The methods provide a means of both maintaining sporastatic conditions in *Bacillus* spore suspensions, as well as preventing spoilage of the liquid suspensions at ambient temperatures, including spoilage at room temperature. The sporastatic suspensions prepared according to the methods of the invention are useful for industrial applications, including environmental, agricultural, food, and feed applications; for example applications such as soil conditioning, antifungal treatment of plants, as a food or feed additive or preservative, and as a deodorant for feces and urine of animals.

For the purposes of the invention, as used herein, by "sporastatic conditions" is meant conditions that determinably prevent and/or inhibit germination and growth of the spores into enabled *Bacillus*; by "enabled *Bacillus*" is meant non-dormant *Bacillus* capable of germination and growth to a vegetative state; by "spoilage" is meant growth of unwanted microorganisms. For the purposes of the invention, as used herein, the term "plant" includes seeds or any growing portion of a higher plant, including, for example, roots, shoots, leaves, and the like. For the purposes of the invention, as used herein, the term "plant material" includes any material derived or harvested from a plant, including for example, leaves, roots, shoots, fruit, seeds, and the like; as well as foods and feeds.

Particular embodiments of the invention comprise suspending *Bacillus* spores in a liquid consisting essentially of water and acetic acid, wherein the acetic acid lowers the pH so that the spores are inhibited from germination and growth, as stated above. It is recognized that the particular order of combining water, acetic acid, and the spores, is not limiting, so long as the stated lowering of the pH, and/or concentration of the acetic acid is achieved. For example, the invention encompasses preparing a desired dilution of acetic acid by combining acetic acid and water, and thereafter combining the spores with the diluted acetic acid. Alternatively, the spores can be combined with water to produce a suspension and a desired amount of concentrated acetic acid added to the suspension. Regardless of the particular order, the pH can be monitored as needed, including the pH of the final sporastatic spore suspension.

It is envisioned that the sporastatic suspensions comprising the *Bacillus* spores are suitable for storage at ambient temperatures, including room temperature. The shelf life of the suspensions can be determined by methods well known in the art, and as otherwise illustrated or described herein; such as by visual inspection for gross contamination; microscopic examination to determine spoilage such as unwanted bacterial, fungal, yeast or mold growth; microscopic examination to confirm maintenance of spores (i.e. confirmation of inhibition of continued inhibition of germination and growth), and specific assays to determine contamination by other unwanted bacteria, such as gram negative bacteria, and the like. In this regard, the compositions prepared according to the methods of the invention are stable for at least 3 months, six months, one year, and even up to two years from the time of their preparation, when stored at ambient temperatures, including room temperature.

It is recognized that for the purposes of commercial preparation, storage, and/or shelf life study, it is desirable to store the compositions prepared according to the methods of the invention in a sealed container, such as a sealed vessel, a drum, and the like. Thus, in a particular embodiment of the invention, the methods of the invention further comprise sealing a container containing the *Bacillus* spores suspended in a suspension step according to the methods of the invention. In another, the invention encompasses an article of manufacture comprising the sealed container. In another, the article includes directions for use. In another, the directions comprise directions for neutralizing the liquid in said container.

Particular embodiments of the present invention utilize acetic acid from a fermentation process to produce a vinegar. In further embodiments, the acetic acid is from a 20 percent acetic acid vinegar. It is recognized that an advantage of the present invention is the utilization of non-synthetic sources of acetic acid; in other words, acetic acid derived from a fermentation process, rather than a chemical synthesis process. Suitable industrial vinegar preparations for use in the methods and compositions of the invention include, for example, Distilled White Vinegar Concentrate (national Vinegar Co., St Louis Mo.; Product NO. nvc-5034) which is available as a 20% (200 g/l) concentrate.

Other acids suitable for the purposes of the methods and compositions of the invention include other water soluble organic acids. Preferably such water soluble organic acids have a carbon chain length of ten or less; or seven or less. Examples of such suitable organic acids include lactic-, citric-, succinic-, malic-, and formic acid, and the like. It is recognized that the suitable organic acid for the purposes of the invention be of a chain length to have favorable solubility in water, for the purposes of the invention. A particular acid suitable for use in the methods and compositions of the invention is lactic acid, which is well known to be producible by non-synthetic means from lactic acid producing bacteria, including lactobacilli and/or *Pediococcus* which are well known as being suitable for food applications. In particular embodiments of the invention, one or more suitable organic acids are substituted for, or used in combination with acetic acid according to the methods of the invention. Such suitable organic acids are non-toxic for the purposes of the invention; with respect to the bacterial spores and with respect to the particular intended application.

In an aspect of the invention comprising a neutralizing step, in a particular embodiment of the present invention, the neutralizing is with a base selected from the group consisting of: sodium bicarbonate, potassium bicarbonate, sodium hydroxide, potassium hydroxide, calcium carbonate, and alkaline soil. As stated herein, the neutralizing is to enable the *Bacillus* spores to provide an enabled *Bacillus* for application to agricultural soil or plant material. In particular embodiments of the present invention, the methods further comprise applying the enabled *Bacillus* to the soil or plant material. Thus, it is recognized that where the application is to alkaline soil, the neutralizing and the applying steps can be optionally, and conveniently, combined. In other words, where the soil is of sufficient alkalinity to neutralize the acidic liquid in which the sporastatic spores are suspended, the neutralizing of the acidic suspension liquid can be achieved by direct application of the spores suspended according to a suspending step of the invention to the alkaline soil; thereby neutralizing the liquid and providing an enabled *Bacillus* to the soil in the same step. For the purposes of the invention, a pH range of 5.5-8.5 is considered as being sufficiently neutral for most applications requiring a neutral pH, with the pH of 7.0-7.5 being optimal; however, it is recognized that the pH can be optimized in a strain-specific manner depending upon the particular *Bacillus* strain and the type of application desired. The invention encompasses all variations of the neutralizing step that bring about an enabled *Bacillus* for application to soil, plant or plant material.

In any aspect of the invention comprising an optional washing step, the washing is achieved by utilization of water, or an organic acid diluted for the purposes of washing, including for example acetic acid diluted for use in a suspending step of the invention. The particular choice of the wash liquid, the manner and number of washes can be optimized by the ordinarily skilled artisan, for the purposes of the invention.

*Bacillus* species particularly suitable for the purposes of the methods and compositions of the invention include the *B. subtilis, B. amyloliquefaciens, B. atropheus, B. mojavensis*, and *B. spizizenii*; and the invention encompasses particular embodiments in which the *Bacillus* is selected from one or more of these species. Depending on the particular application desired, other such suitable species of *Bacillus* include non-pathogenic *B. megaterium, B. pumilus, B. simplex, B. licheniformis, B. sonorensis, B. vietnamensis, B. acidicola, B. oleronius*, and *B. cereus, B. circulars, B. polymyxa, B. coagulans*, and *B. macetans*. The particular species and/or strains selected are non-pathogenic for the purposes of the particular application; and include natural and/or modified strains. For the purposes of the invention, as used herein, by "modified" is intended a strain harboring a plasmid, or recombinant strains in which heterologous nucleic acid is integrated into the bacterial genome by recombinant methods.

The invention provides methods for providing *Bacillus* spores for application to agricultural soil or plant material, and particular embodiments of the invention comprise applying the enabled *Bacillus* to the soil or plant material. The application is achieved by any method known to the ordinarily skilled artisan to bring an effective amount of the *Bacillus* spores into contact with the plant, plant material or soil, for the intended purpose of the application. For example, for field applications, the applying can be achieved by spraying, by conducting foliar spray, and the like. Examples of known methods that can be utilized in an applying step of the invention include those described in U.S. Pat. No. 6,589,524; U.S. Pat. No. 6,830,459; and U.S. Pat. No. 6,423,310 for antimicrobial and anti fungal purposes; in U.S. Pat. No. 5,733,355 for soil application purposes; and U.S. Pat. No. 5,919,695 for the purposes of mold control and prevention of spoilage in various materials including foods; the contents of each recited patent is hereby incorporated herein by reference.

The following illustrations are provided by way of example and are not meant to be construed as limiting the invention. Unless otherwise indicated, all numerical ranges provided in the present description are inclusive of the endpoints, and of all numerical values between the endpoints.

EXAMPLES

Example 1: Dry Spore Preparation Characteristics

Where needed for commencing liquid cultures, a dry preparation of *Bacillus* spores having a typical spore count of $100\times10^9$ spores/g is tested for, and found to be free of coagulase positive *staphylococcus, Pseudomonas aeruginosa*, and *Salmonella/Shigella* sp. The preparation is further tested for the presence of yeast and mold, by plating on Potato Dextrose Agar (PDA) and found to contain less than 100 spores/g. The preparation is further tested for the presence of coliforms by plating on Hektoen agar and found to contain less than 100 colony forming units (cfu)/g.

Example 2: Enumeration Procedure

Enumeration of the liquid spore suspensions was performed according to the following procedure. The suspension was distributed to three VWR 1 Liter glass bottles and labeled as Control, 1% Acetic Acid, and 2% Acetic Acid. To create each of the test spore suspensions, an OMRI listed 20% non-synthetic Acetic Acid (nsAA) (National Vinegar Company) was utilized. Before samples were taken, the three containers were shaken vigorously for five minutes using arc-like swings assuring that no precipitate was seen in the bottles. Using a 1 ml sterile pipette, 1 ml was transferred from the spore suspension to a 99 ml dilution buffer bottle labeled $10^{-2}$. Repeatedly, the 1 ml pipette was rinsed with the $10^{-2}$ dilution buffer until the sample was completely removed from the pipette. The $10^{-2}$ dilution bottle was shaken vigorously for one minute using the arm in an arc-like motion. Using another sterile pipette, 1 ml was transferred from the $10^{-2}$ bottle to a 99 ml dilution buffer bottle labeled $10^{-4}$. Repeatedly, the 1 ml pipette was rinsed with the $10^{-4}$ dilution buffer until the sample was completely removed from the pipette. For $10^{-7}$ plating, using an 11 ml sterile pipette, 11 ml was transferred from the $10^{-5}$ bottle to a 99 ml dilution buffer bottle labeled $10^{-6}$. The $10^{-6}$ dilution bottle was vigorously shaken for one minute using the arm in an arc-like motion as described. Using a calibrated micropipette, 100 μl from $10^{-6}$ dilution bottle was transferred onto four dry Trypticase Soy Agar (TSA) plates. All plates were incubated at 37° C. and counted after 24 hours of incubation. The counts are reported as spores per milliliter (spores/ml). All three samples were struck for isolation on Hektoen and MacConkey agar at 35° C. and 25° C. respectively for 48 hours, to serve as an indicator of unwanted growth in the spore suspensions. As gram positive organisms, such as members of the Genus *Bacillus*, are incapable of growth on these selective media, presence of any growth indicates inefficient stabilization.

Example 3: Preparation and Testing of *Bacillus subtilis* Spore Suspensions

*Bacillus subtilis* spores were prepared in a stainless steel bioreactor using a minimal media for spore production*, as is well known in the art. Media was autoclaved at 121° C. for 30 minutes prior to inoculation. Seed culture was inoculated at 1%, incubated at 35° C. and agitated at 250 rpm under aeration for 24-72 hours. Samples were examined microscopically over this period to detect the formation of endospores. When 90-100% sporulation was visually detected, typically corresponding to $5\times10^8$ to $5\times10^{10}$ spores/ml, the spore broth was concentrated via tangential flow microfiltration using a Millipore Pellicon system (Millipore Corporation, Billerica, Mass.) with a 0.1 micron Pellicon 2 mini filter (cat.# P2B01MV01). Typically, the microfiltration was continued until the concentration of the spores in the medium was about 8-10 times in comparison to the spore concentration in the beginning of the filtration. The resulting spore slurry, was divided into three non-sterile vessels labeled Control, 1% nsAA (non-synthetic Acetic Acid), and 2% nsAA. An OMRI (Organic Materials Review Institute)—listed 20% nsAA (National Vinegar Company) was respectively added to create each of test spore suspensions, while de-ionized water was used to make up the volume difference in the control and test suspensions. Typically, the spores were suspended in the indicated concentrations of acetic acid to a final count of $1\times10^9$ to $1\times10^{11}$ spores/ml. All three samples were enumerated using the enumeration procedure set forth above, and struck for isolation on Hektoen and MacConkey agars, incubated at 35° C. and 25° C. respectively, to serve as an indicator of unwanted growth in the spore suspensions. As gram positive organisms, such as members of the Genus *Bacillus*, are incapable of growth on these selective media, presence of any growth indicates inefficient inhibition of unwanted microbial growth.

*Minimal Media for spore production (percentages represent weight/volume):

0.1-2% D-Monosaccharide (Dextrose, D-Fructose, D-Mannose, or D-Galactose); or sucrose or starch
0.1-2% Yeast Extract
0.1-2% Vegetable Peptone (soy, wheat, or pea); or Corn Steep Liquor
0.5% Sodium or potassium salt (NaCl, KCl, NaBr, or KBr)
0.01-0.05% Each of $Mg^{++}$; $Mn^{++}$; $Ca^{++}$; $Fe^{++}$; and $Zn^{++}$ salts ($MgCl_2$, $MnCl_2$, $CaCl_2$, $FeSO_4$, $ZnSO_4$)

The results depicted in FIG. 1 indicate that under the conditions tested, the spore suspensions suspended in 1% or 2% nsAA are stable for at least 88 days. Plating of the samples on Hektoen-, MacConkey, and Potato Dextrose agar plates as explained above, indicates that the spore preparations in 1% or 2% nsAA are free of unwanted microorganisms.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:

1. A method for providing a *Bacillus* on agricultural soil or plant material, which comprises the steps of:
   (a) suspending *Bacillus* spores in a liquid consisting essentially of water and acetic acid, wherein the acetic acid lowers the pH so that the spores are inhibited from germination and growth, and wherein the liquid does not contain a synthetic chemical; and;
   (b) neutralizing the liquid of step (a) to enable the spores to provide an enabled *Bacillus* and applying the enabled *Bacillus* to the soil or plant material, wherein the neutralizing step is with an alkali metal base, an alkaline earth metal base, and/or alkaline soil.

2. The method of claim 1 wherein the pH in step (a) is lowered to a pH from about 3.8 to about 4.2.

3. The method of claim 1 wherein the *Bacillus* spores are *Bacillus subtilis*.

4. The method of claim 1 wherein the plant material in step (b) is a seed.

5. The method of claim 1 wherein the applying in step (b) is to soil.

6. The method of claim 1 wherein the applying in step (b) is to a plant.

7. The method of claim 1 wherein the base is selected from the group consisting of: sodium bicarbonate, potassium bicarbonate, sodium hydroxide, potassium hydroxide, and calcium carbonate.

8. The method of claim 1 wherein the acetic acid is from a fermentation process to produce vinegar used in step (a).

9. The method of claim 1 wherein the acetic acid is from a 20 percent acetic acid vinegar which is used to lower the pH in step (a).

10. The method of claim 1 wherein the acetic acid in said liquid is at a concentration of 1 to 5%.

11. A method for providing a *Bacillus* on agricultural soil or plant material, which comprises the steps:
    (a) preparing *Bacillus* spores in a minimal media effective to sporulate *Bacillus*;
    (b) separating said spores from said media;
    (c) optionally washing said spores;
    (d) suspending the spores from step (b) or (c) in a liquid consisting essentially of water and acetic acid, wherein the acetic acid lowers the pH so that the spores are inhibited from germination and growth, and wherein the liquid does not contain a synthetic chemical; and
    (e) neutralizing the liquid of step (d) to enable the spores to provide an enabled *Bacillus* and applying the enabled *Bacillus* to the soil or plant material, wherein the neutralizing step is with an alkali metal base, an alkaline earth metal base, and/or alkaline soil.

12. The method of claim 11, wherein said separating is by tangential flow filtration or centrifugation.

13. The method of claim 12, wherein said tangential flow filtration utilizes a filter from about 0.1 micron to less than 1 micron.

14. The method of claim 12, wherein said centrifugation is performed at a force from about 3,000 g to about 10,000 g.

15. The method of claim 11 wherein the pH is lowered to a pH from about 3.8 to about 4.2.

16. The method of claim 11 wherein the *Bacillus* spores are *Bacillus subtilis*.

17. The method of claim 11 wherein the plant material is a seed.

18. The method of claim 11 wherein the application is to soil.

19. The method of claim 11 wherein the application is to a plant.

20. The method of claim 11, wherein the acetic acid in said liquid is at a concentration of 1 to 5%.

21. A method for providing a *Bacillus* on agricultural soil or plant material, which comprises the steps:
    (a) suspending *Bacillus* spores in a liquid consisting essentially of water and an organic acid, wherein the organic acid lowers the pH so that the spores are inhibited from germination and growth, and wherein the liquid does not contain a synthetic chemical; and
    (b) neutralizing the liquid of step (a) to enable the spores to provide an enabled *Bacillus* and applying the enabled *Bacillus* to the soil or plant material, wherein the neutralizing step is with an alkali metal base, an alkaline earth metal base, and/or alkaline soil.

22. The method of claim 21, further comprising the steps of:
    i) preparing *Bacillus* spores in a minimal media effective to sporulate *Bacillus*;
    ii) separating said spores from said media; and
    iii) optionally washing said spores;
    wherein said steps (i), (ii), and (iii) are performed prior to the suspending step.

\* \* \* \* \*